United States Patent
Bar Shalom

(10) Patent No.: US 8,142,193 B2
(45) Date of Patent: Mar. 27, 2012

(54) COMPOUND ANGULAR JOINT FOR CONNECTING AN ABUTMENT TO A DENTAL IMPLANT IN A PREDEFINED ANGLE

(76) Inventor: Eliezer Bar Shalom, Nir Galim (IL)

( * ) Notice: Subject to any disclaimer, the term of this patent is extended or adjusted under 35 U.S.C. 154(b) by 196 days.

(21) Appl. No.: 12/491,322

(22) Filed: Jun. 25, 2009

(65) Prior Publication Data

US 2010/0330529 A1    Dec. 30, 2010

(51) Int. Cl.
*A61C 8/00* (2006.01)
(52) U.S. Cl. .................................................... 433/173
(58) Field of Classification Search ............... 433/173, 433/174
See application file for complete search history.

(56) References Cited

U.S. PATENT DOCUMENTS

| | | | |
|---|---|---|---|
| 5,030,095 A * | 7/1991 | Niznick | 433/173 |
| 5,069,622 A | 12/1991 | Rangert et al. | |
| 5,116,225 A | 5/1992 | Riera | |
| 5,417,570 A | 5/1995 | Zuest et al. | |
| 5,662,474 A | 9/1997 | Jorneus et al. | |
| 5,904,483 A | 5/1999 | Wade | |
| 6,093,023 A | 7/2000 | Meseguer | |
| 2006/0024644 A1 | 2/2006 | Cohen | |
| 2009/0117520 A1 | 5/2009 | Kikuchi | |
| 2011/0097687 A1 * | 4/2011 | Engman | 433/174 |

FOREIGN PATENT DOCUMENTS

EP    2168531    3/2010

OTHER PUBLICATIONS

International Search Report of the International Searching Authority (ISA/US) dated Nov. 22, 2010 for the corresponding PCT application No. PCT/IB2010/052822.
Written Opinion of the International Searching Authority (ISA/US) dated Nov. 22, 2010 for the corresponding PCT application No. PCT/IB2010/052822.
Search Report for the corresponding European Patent Application No. 10167044.6 dated Oct. 19, 2010.

* cited by examiner

*Primary Examiner* — Cris L Rodriguez
*Assistant Examiner* — Eric Rosen
(74) *Attorney, Agent, or Firm* — The Law Office of Michael E. Kondoudis

(57) ABSTRACT

A compound angular joint for connecting an abutment to a dental implant in a predefined angle. One compound angular joint includes a basal member connectable to the dental implant, and an apical member connectable to the abutment. The apical member is connected to the basal member forming the predefined angle. Assembling the compound angular joint of the two members allows achieving a strong and stable connection between the basal member and the dental implant, between the apical member and the abutment, and between the basal member and the apical member. The compound angular joint may be used in prostheses to allow optimally exploiting the bone structure of the jaw.

8 Claims, 6 Drawing Sheets

COMPOUND ANGULAR JOINT FOR CONNECTING AN ABUTMENT TO A DENTAL IMPLANT IN A PREDEFINED ANGLE

BACKGROUND

1. Technical Field

The present invention relates to the field of dentistry, and more particularly, to a dental connector.

2. Discussion of Related Art

Attaching abutments to dental implants necessitates a compromise between the preferred positions of the abutments and the possible locations for implanting the dental implants. This compromise is required as the position of the dental implants in the jaw dictates the positions and directions of the abutments, while considerations relating to the prosthesis imply other requirements regarding the positions and directions of the abutments.

BRIEF SUMMARY

Embodiments of the present invention provide a compound angular joint for connecting an abutment to a dental implant in a predefined angle. One compound angular joint comprises: a basal member having a first length axis and comprising a distal inner thread having a second length axis; and an apical member comprising an apical member distal inner thread, and a proximal outer thread corresponding to the distal inner thread of the basal member and exhibiting the second length axis upon connection thereto. The basal member has a hole having a predefined shape and going through the basal member, such that the basal member has an inner surface, wherein the hole allows proximally connecting the basal member to the dental implant by inserting an implant connector through the hole and connecting the implant connector to the dental implant, and wherein the distal inner thread is located distally on the inner surface and comprises at least two complete windings. The predefined shape is selected such that it allows fastening the basal member to the dental implant by the implant connector. The apical member is distally connectable to the abutment by connecting an abutment connector to the apical member distal inner thread. The apical member distal inner thread comprises at least two complete windings, such that the at least two complete windings allow securing the abutment to the apical member by the abutment connector. The second length axis forms the predefined angle to the first length axis.

Embodiments of the present invention provide a system for enhancing the flexibility of prosthesis implantation onto a jaw. One system comprises: at least one dental implant implantable in the jaw in predefined implant locations; at least one abutment connectable to the prosthesis in predefined locations and angles selected in correspondence to the predefined implant locations, each abutment forming a predefined angle with the corresponding dental implant; and at least one compound angular joint arranged to connect at least one abutment with the predefined angle differing from 180° to the corresponding dental implant. One compound angular joint comprises: a basal member having a first length axis and comprising a distal inner thread having a second length axis; an apical member comprising an apical member distal inner thread, and a proximal outer thread corresponding to the distal inner thread of the basal member and exhibiting the second length axis upon connection thereto; an implant connector arranged to connect the basal member to the dental implant; and an abutment connector arranged to connect the apical member to the abutment. The basal member has a hole going through the basal member, such that the basal member has an inner surface, wherein the hole allows proximally connecting the basal member to the dental implant by inserting the implant connector through the hole and connecting the implant connector to the dental implant, and wherein the distal inner thread is located distally on the inner surface and comprises at least two complete windings. The apical member is distally connectable to the abutment by connecting the abutment connector to the apical member distal inner thread. The apical member distal inner thread comprises at least two complete windings, such that the at least two complete windings allow securing the abutment to the apical member by the abutment connector. The second length axis forms the predefined angle to the first length axis. The predefined angles of the compound angular joints are selected such as to allow optimal anchoring of the prosthesis in the jaw, thereby allowing a high flexibility in selecting the predefined locations of the dental implants in respect to the jaw structure.

Embodiments of the present invention provide a method of connecting an abutment to a dental implant in a predefined angle. One method comprises: attaching a basal member to the dental implant; attaching an apical member to the basal member at the predefined angle; and attaching the abutment to the apical member.

Embodiments of the present invention provide a method of connecting a prosthesis to a jaw with a given bone structure. One method comprises: implanting a plurality of dental implants into the jaw; defining predefined angles for a plurality of abutments supporting the prosthesis in respect to the dental implants, such that each abutment corresponds to a dental implant; for at least one of the abutments, for which the predefined angle is different from 180°; attaching a basal member to the dental implant, attaching an apical member to the basal member at the predefined angle, and attaching the abutment to the apical member; and attaching abutments to dental implants which require predefined angles of 180°; and connecting the prosthesis to the abutments. The implanting the dental implants into the jaw is carried out in respect to the jaw's bone structure exclusively.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which.

DETAILED DESCRIPTION

Figure 1:
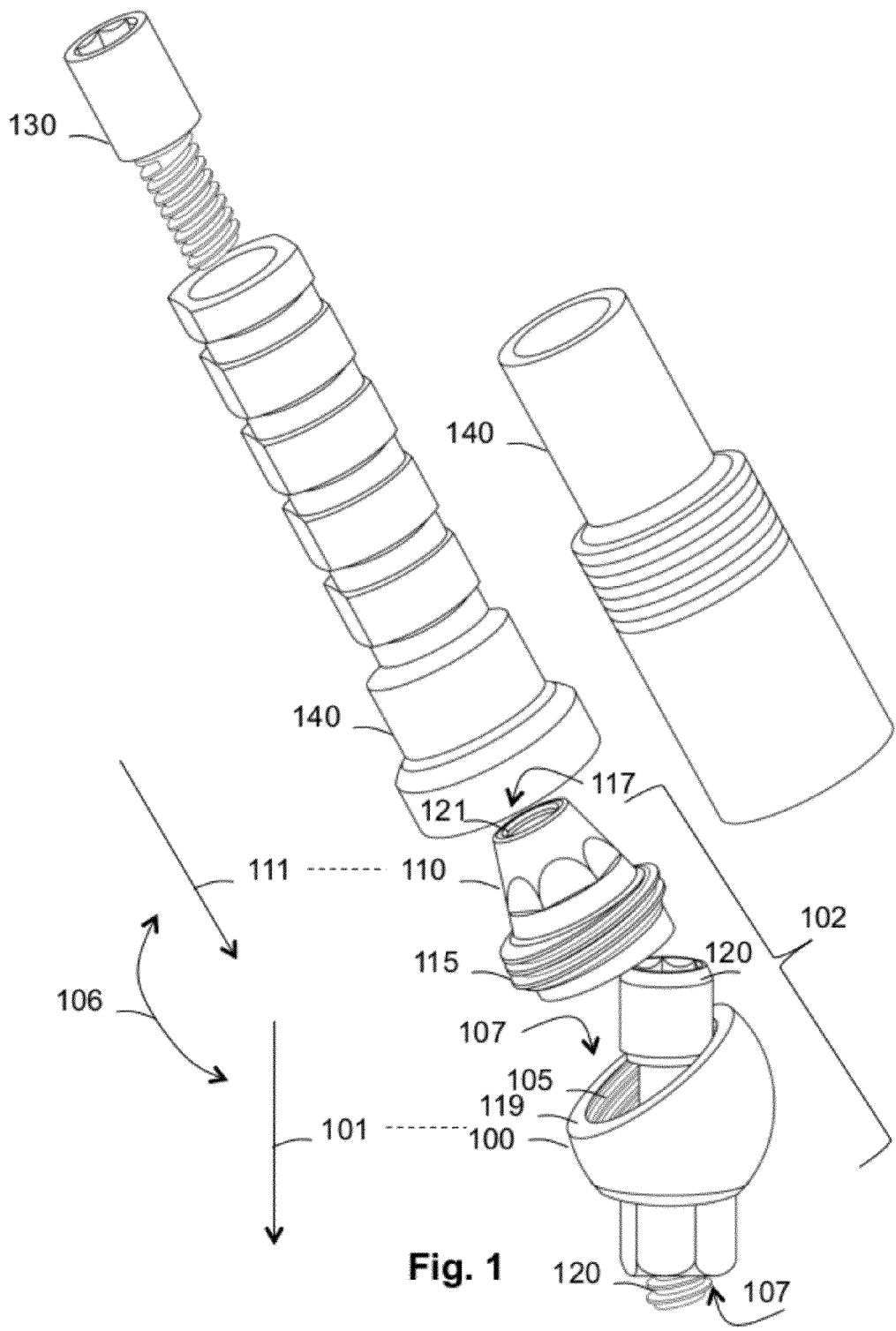
FIGS. 1, 2 and 3 are high level schematic illustrations of a compound angular joint for connecting an abutment to a dental implant in a predefined angle, according to some embodiments of the invention.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 2:
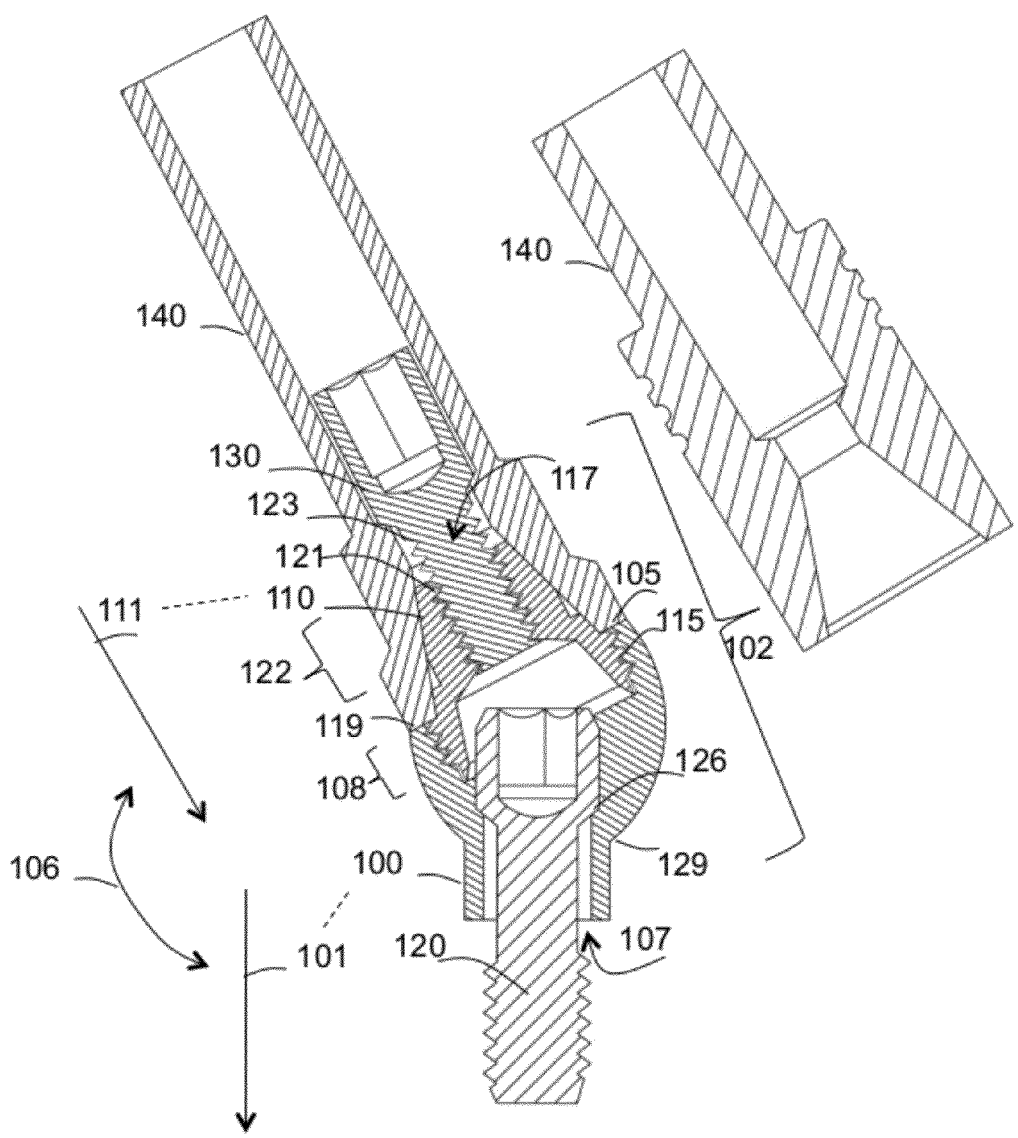
Figure 3:
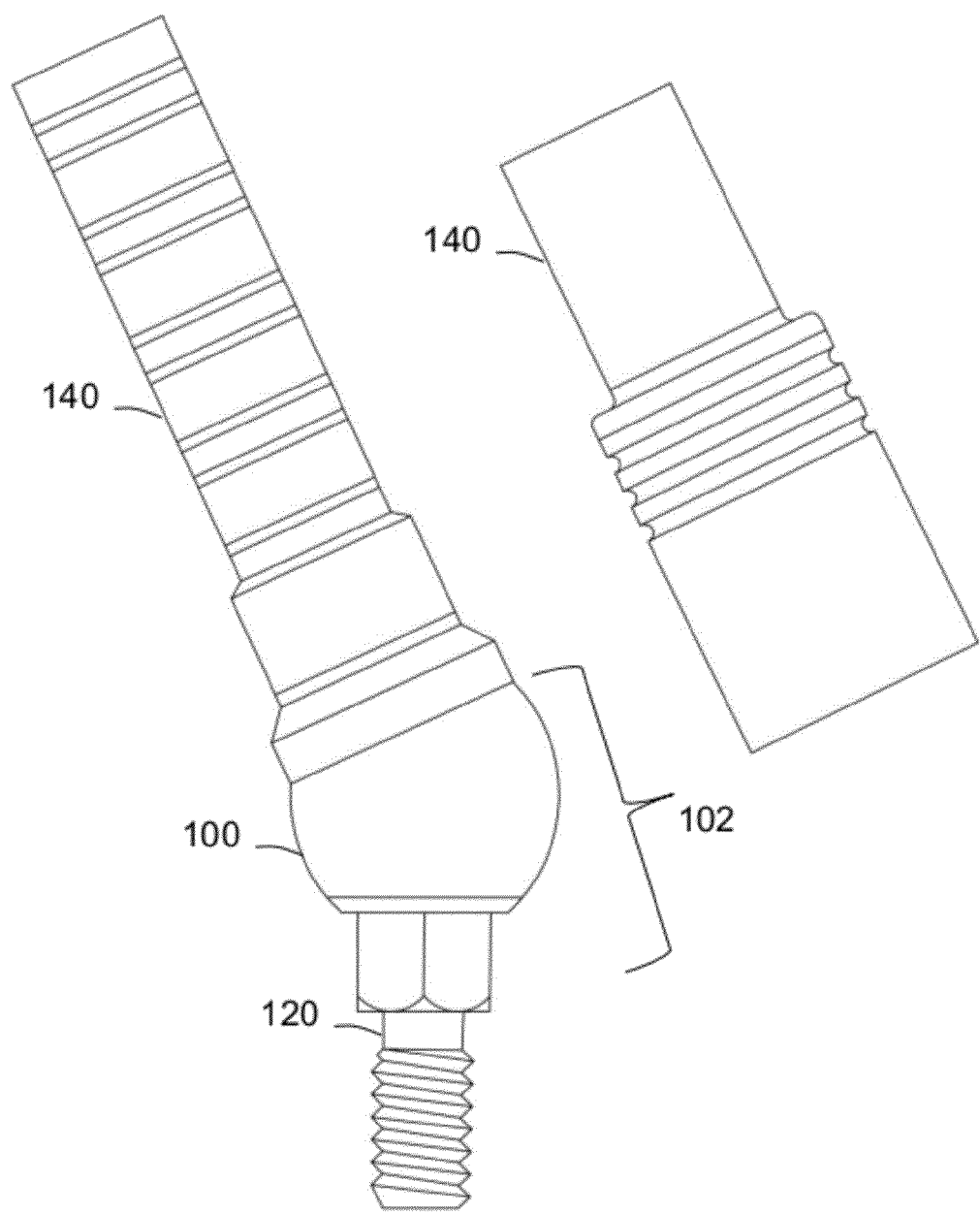

FIGS. 1, 2 and 3 are high level schematic illustrations of a compound angular joint 102 for connecting an abutment 140 to a dental implant in a predefined angle 106, according to some embodiments of the invention. FIG. 1 is an exploded perspective view, FIG. 2 is a cross section view of compound angular joint 102, and FIG. 3 is a side view of compound angular joint 102. Compound angular joint 102 comprises a basal member 100 and an apical member 110. Basal member 100 has a first length axis 101 and comprises a distal inner thread 105 having a second length axis 111. Apical member 110 comprises an apical member distal inner thread 121 and a proximal outer thread 115 corresponding to distal inner thread 105 of basal member 100 and exhibiting second length axis 111 upon connection to basal member 100. Basal member 100 is proximally connectable to the dental implant (not shown) and apical member 110 is distally connectable to abutment 140. Basal member 100 has a hole 107 having a predefined shape and going through basal member 100, such that basal member 100 has an inner surface. Hole 107 allows proximally connecting basal member 100 to the dental implant by inserting an implant connector 120 through hole 107 and connecting implant connector 120 to the dental implant, e.g., by fastening a head of implant connector 120 against the inner surface of basal member 100. The predefined shape is selected such as to support implant connector 120 and allow its fastening onto basal member 100 and to the dental implant (e.g., when implant connector 120 is a screw, by a shoulder 126 shaped to support the head of the screw). Basal member 100 may comprise a shoulder 119 in hole 107 that is wide enough to operatively support abutment 140 when connected via apical member 110 thereto. The outer form of basal member 100 is arranged to fit into the dental implant, e.g., have a shoulder 129 in the form of a truncated cone fitting into a part of the socket of the dental implant.

Distal inner thread 105 is located distally on the inner surface and comprises at least two complete windings 108. The number of complete windings is determined by the geometry of hole 107. At least two complete windings 108 are necessary for securing apical member 110 to basal member 100. The number of complete windings may reach three or four windings, such as to firmly support abutment 140. Additional windings of distal inner thread 105 may be partial (incomplete in their proximal part due to a boring for implant connector 120 that is part of hole 107), yet contribute some holding force to connecting apical member 110 to basal member 100. Distal inner thread 105 may further comprise fastening means (such as a lock tight material) for holding apical member 110 in place connected to basal member 100 and resist loosening of contact between proximal outer thread 115 of apical member 110 and distal inner thread 105 of basal member 100.

Apical member 110 is distally connectable to abutment 140 by connecting an abutment connector 130 to apical member distal inner thread 121. Apical member distal inner thread 121 comprises at least two complete windings, such that the at least two complete windings 122 that allow securing abutment 140 to apical member 110 by abutment connector 130. Two versions of abutment 140 are presented in FIGS. 1, 2 and 3, for example a titanium, or a plastic abutment with different forms and relating to different methods of attachment to the prosthesis. Second length axis 111 forms predefined angle 106 to first length axis 101. Predefined angle 106 between abutment 140 and the distal implant allows better use of the existing bone masses in the jaw to fixate a prosthesis upon abutment 140, and allow greater flexibility in fitting an appropriate prosthesis to jaws that may be wanting in respect to the bone structure they present. For example, predefined angle 106 may allow connecting incisor prostheses which are often difficult to implant and support when dental implant and abutment 140 form a 180° angle. As examples, predefined angle 106 may comprise standard angles such as 17° and 30°.

According to some embodiments of the invention, compound angular joint 102 may further comprise implant connector 120 arranged to connect basal member 100 to the dental implant (not shown), and abutment connector 130 arranged to connect apical member 110 to abutment 140.

According to some embodiments of the invention, apical member 110 has a hole 117 going through apical member 110 and comprises an apical member distal inner thread 121 that allows connecting apical member 110 to abutment 140 by abutment connector 130. Apical member distal inner thread 121 is located distally on the inner surface of hole 117 and comprises at least two complete windings 122. The number of complete windings 122 is determined by the geometry of hole 117. At least two complete windings 122 are necessary for securing abutment 140 to apical member 110. The number of complete windings 122 may reach three or four windings, such as to firmly support abutment 140. Additional windings of apical member distal inner thread 121 may be partial (incomplete in their proximal part due to a boring for implant connector 120 that is part of hole 107), yet contribute some holding force to connecting abutment 140 to apical member 110. Apical member distal inner thread 121 may further comprise fastening means (such as a lock tight material) for holding abutment 140 in place connected to apical member 110 and resist loosening of contact between an outer thread 123 of abutment connector 130 and apical member distal inner thread 121 of apical member 110.

According to some embodiments of the invention, assembling compound angular joint 102 from two parts, namely basal member 100 and apical member 110 allows having enough complete windings 122 to support abutment 140. This is a substantial improvement in respect to conventional angular connectors, in which the space left for a connector to the dental implant cuts a substantial part out of the thread that is used to connect the abutment to the connector. Due to this, conventional angular connectors offer a weak support to the abutment. In contrast, embodiments of the disclosed invention allow a much better connection to abutment 140 due to the larger number of complete windings 122.

According to some embodiments of the invention, abutment connector 130 and implant connector 120 may be screws. Basal member 100 is shaped to hold the screw head of implant connector 120, while basal member 100 and apical member 110 are shaped such as to allow their connection when basal member 100 is connected to the dental implant by implant connector 120, i.e., leaving place for the screw head. This shaping basal member 100 and apical member 110 may be selected such as to allow connecting them at a predefined angle 106 ranging between 90° and 180°. Forms of basal member 100 and apical member 110 may change according to the required predefined angle 106. Compound angular joint 102, basal member 100, apical member 110 or their form of connection may be selected or arranged to allow adjusting predefined angle 106 between second length axis 111 and first length axis 101.

Figure 4:
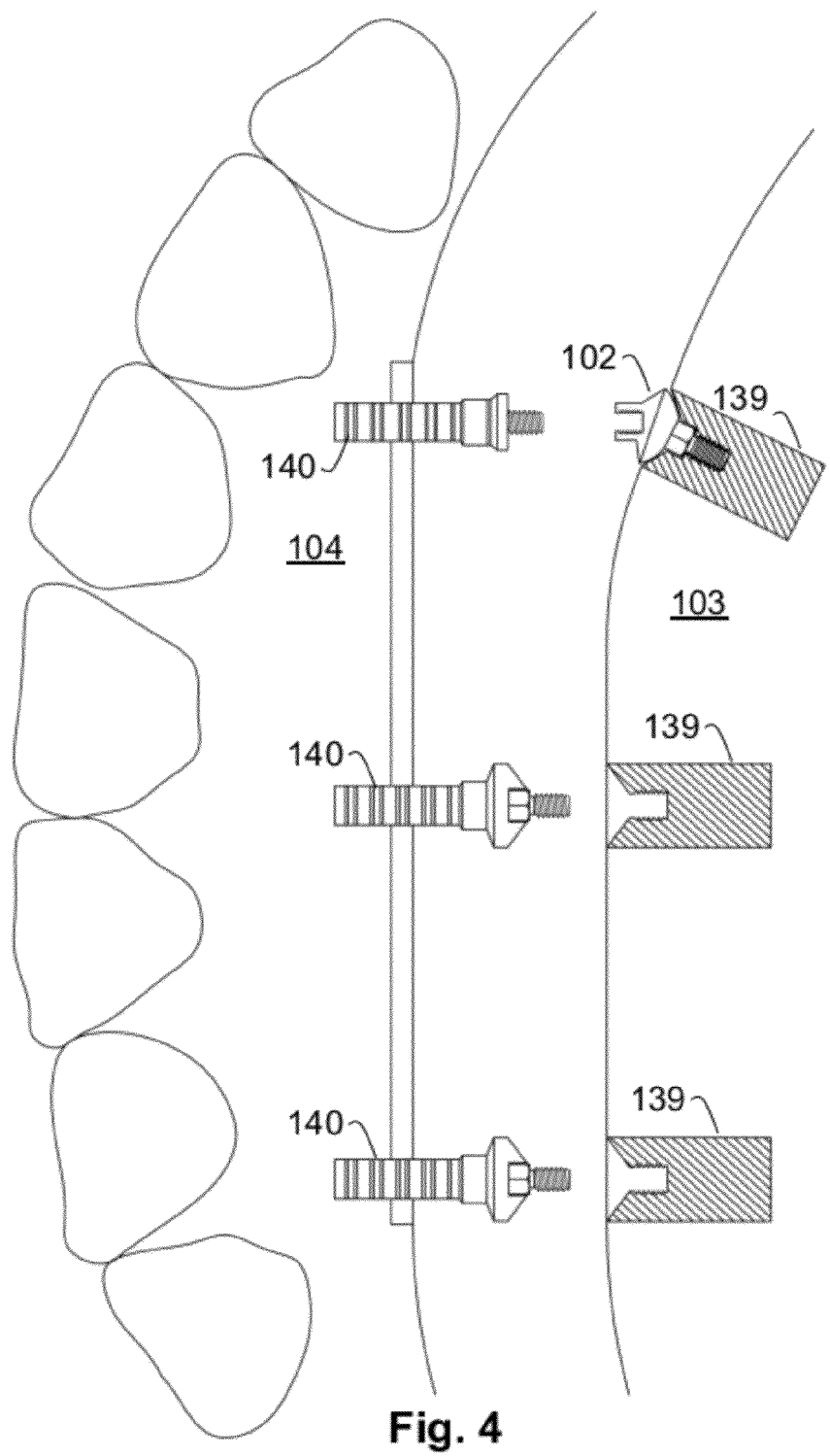
FIG. 4 is a high level schematic illustration of a system for enhancing the flexibility of prosthesis implantation onto a jaw, according to some embodiments of the invention.

FIG. 4 is a high level schematic illustration of a system 103 for enhancing the flexibility of prosthesis implantation onto a jaw (not shown), according to some embodiments of the invention. System 103 comprises at least one dental implant 139 implantable in the jaw in predefined implant locations; at least one abutment 140 connectable to a prosthesis 104 in predefined locations and angles selected in correspondence to the predefined implant locations, each abutment forming a predefined angle with the corresponding dental implant; at least one compound angular joint 102 arranged to connect at least one of abutments 140 with predefined angle 106 differing from 180° to corresponding dental implant 139.

Each compound angular joint 102 (see detailed numbering in FIGS. 1 and 2) comprises: basal member 100; apical member 110; implant connector 120 arranged to connect basal member 100 to dental implant 139; and abutment connector 130 arranged to connect apical member 110 to abutment 140. Basal member 100 has a first length axis 101 and comprises a distal inner thread 105 having a second length axis 111. Apical member 110 comprises an apical member distal inner thread 121 and a proximal outer thread 115 corresponding to distal inner thread 105 of basal member 100 and exhibiting second length axis 111 upon connection to basal member 100. Basal member 100 is proximally connectable to the dental implant (not shown) and apical member 110 is distally connectable to abutment 140. Basal member 100 has a hole 107 having a predefined shape and going through basal member 100, such that basal member 100 has an inner surface. Hole 107 allows proximally connecting basal member 100 to the dental implant by inserting an implant connector 120 through hole 107 and connecting implant connector 120 to the dental implant, e.g., by fastening a head of implant connector 120 against the inner surface of basal member 100. The predefined shape is selected such as to support implant connector 120 and allow its fastening onto basal member 100 and to the dental implant. Basal member 100 may comprise a shoulder 119 in hole 107 that is wide enough to operatively support abutment 140 when connected via apical member 110 thereto. Distal inner thread 105 is located distally on the inner surface and comprises at least two complete windings 108. The number of complete windings is determined by the geometry of hole 107. At least two complete windings 108 are necessary for securing apical member 110 to basal member 100. The number of complete windings may reach three or four windings, such as to firmly support abutment 140. Additional windings of distal inner thread 105 may be partial (incomplete in their proximal part due to a boring for implant connector 120 that is part of hole 107), yet contribute some holding force to connecting apical member 110 to basal member 100. Distal inner thread 105 may further comprise fastening means (such as a lock tight material) for holding apical member 110 in place connected to basal member 100 and resist loosening of contact between proximal outer thread 115 of apical member 110 and distal inner thread 105 of basal member 100. Apical member 110 is distally connectable to abutment 140 by connecting an abutment connector 130 to apical member distal inner thread 121. Apical member distal inner thread 121 comprises at least two complete windings, such that the at least two complete windings 122 that allow securing abutment 140 to apical member 110 by abutment connector 130. Second length axis 111 forms predefined angle 106 to first length axis 101. Predefined angle 106 between abutment 140 and the distal implant allows better use of the existing bone masses in the jaw to fixate a prosthesis upon abutment 140, and allow greater flexibility in fitting an appropriate prosthesis to jaws that may be wanting in respect to the bone structure they present.

Each compound angular joint 102 may be arranged to have a different predefined angle 106 in relation to the bone structure of the jaw and the required positioning of abutments 140 and the prosthesis. Predefined angles 106 of compound angular joint 102 are selected such as to allow optimal anchoring of the prosthesis in the jaw, thereby allowing a high flexibility in selecting the predefined locations of the dental implants in respect to the jaw structure. Other connections between other abutments 140 and dental implants 130 may be standard straight connectors or be lacking, such that abutment 140 is connected directly to corresponding dental implant 139. Abutment 140 may have different structures and shapes. The structure may include only one part and the shape may have spherical shape such as a ball.

Predefined angles 106 of compound angular joints 102 may be selected such as to allow optimal anchoring of prosthesis 104 in the jaw, thereby allowing a high flexibility in selecting the predefined locations of dental implants 139 in respect to the jaw structure.

The use of compound angular joint 102 in system 103 may allow implanting dental implants 139 in novel and more stable arrangements such as the "all on four" method comprising implanting dental implants 139 in crossing directions to avoid slipping of prosthesis 104 off dental implants 139 when these are implanted in a parallel manner. The use of compound angular joint 102 further allows substantial tolerance in attaching prosthesis 104 onto dental implants 139 due to the higher flexibility in placing them.

System 103 may comprise any number of compound angular joint 102 with various predefined angles 106, for all necessary predefined angles 106 differing from 180°. Straight connectors or direct connections with appropriate abutments 140 may be used for predefined angles 106 equaling 180°.

According to some embodiments of the invention, each compound angular joint 102, basal member 100, apical member 110 or their form of connection may be selected or arranged to allow adjusting predefined angle 106 between second length axis 111 and first length axis 101. Any compound angular joint 102 may further comprise fastening means for fastening basal member 100 to apical member 110 and apical member 110 to the corresponding abutment 140.

According to some embodiments of the invention, compound angular joint 102 may be used to fit a temporary prosthesis to dental implants 139 and generate a permanent prosthesis according to the temporary prosthesis.

Figure 5:
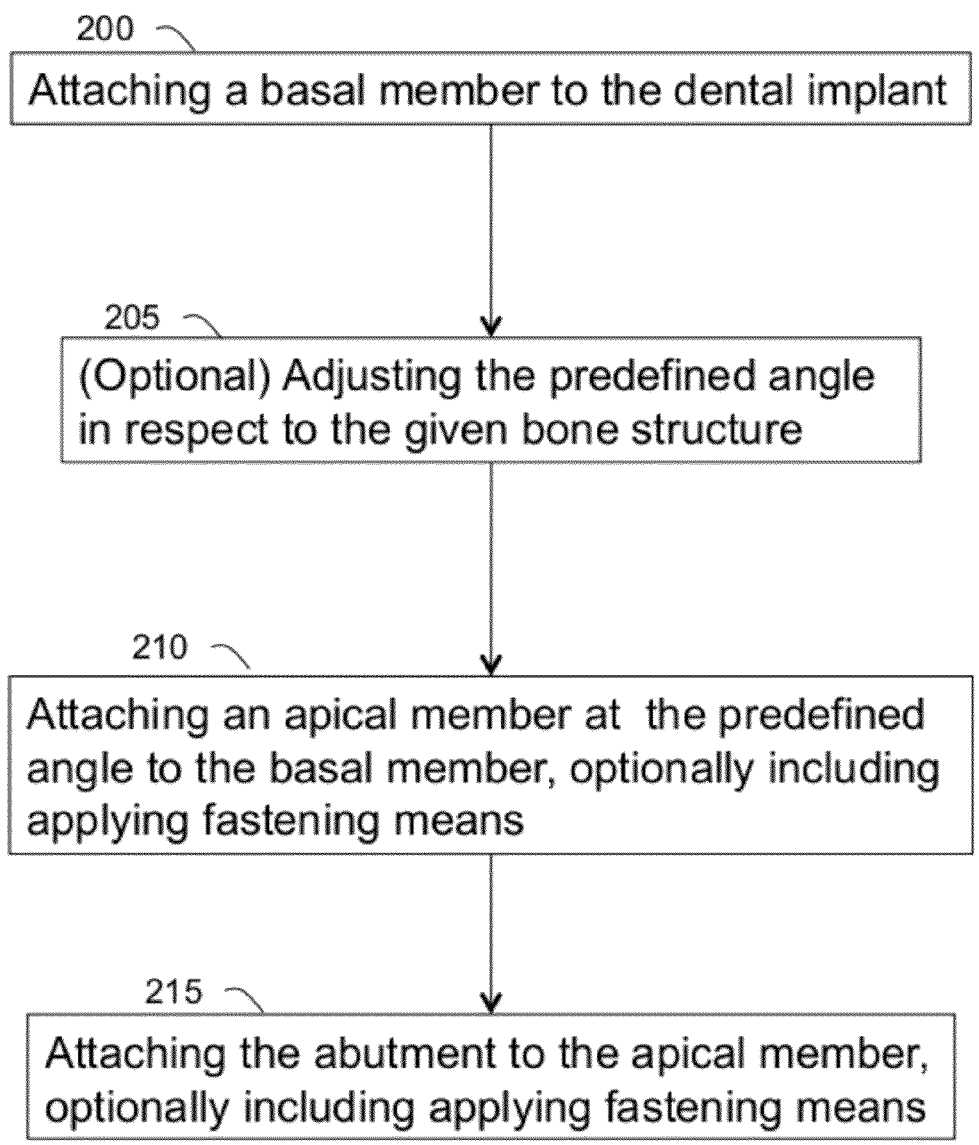
FIG. 5 is a high level schematic flowchart of a method of connecting an abutment to a dental implant in a predefined angle, according to some embodiments of the invention.

FIG. 5 is a high level schematic flowchart of a method of connecting an abutment to a dental implant in a predefined angle, according to some embodiments of the invention. The method comprises the stages: attaching a basal member to the dental implant (stage 200), the basal member comprising a distal inner thread exhibiting a first length axis; attaching an apical member to the basal member (stage 210), the apical member comprising a proximal outer thread corresponding to the distal inner thread of the basal member and exhibiting a second length axis upon the attaching (stage 210); and attaching the abutment to the apical member (stage 215). The second length axis forms the predefined angle to the first length axis. Stage 210 and stage 215 may further comprise applying fastening means to secure the attachments of the apical member to the basal member and of the abutment to the apical member.

According to some embodiments of the invention, the method further comprises adjusting the predefined angle in respect to the given bone structure of the jaw the dental implant is implanted in.

Figure 6:
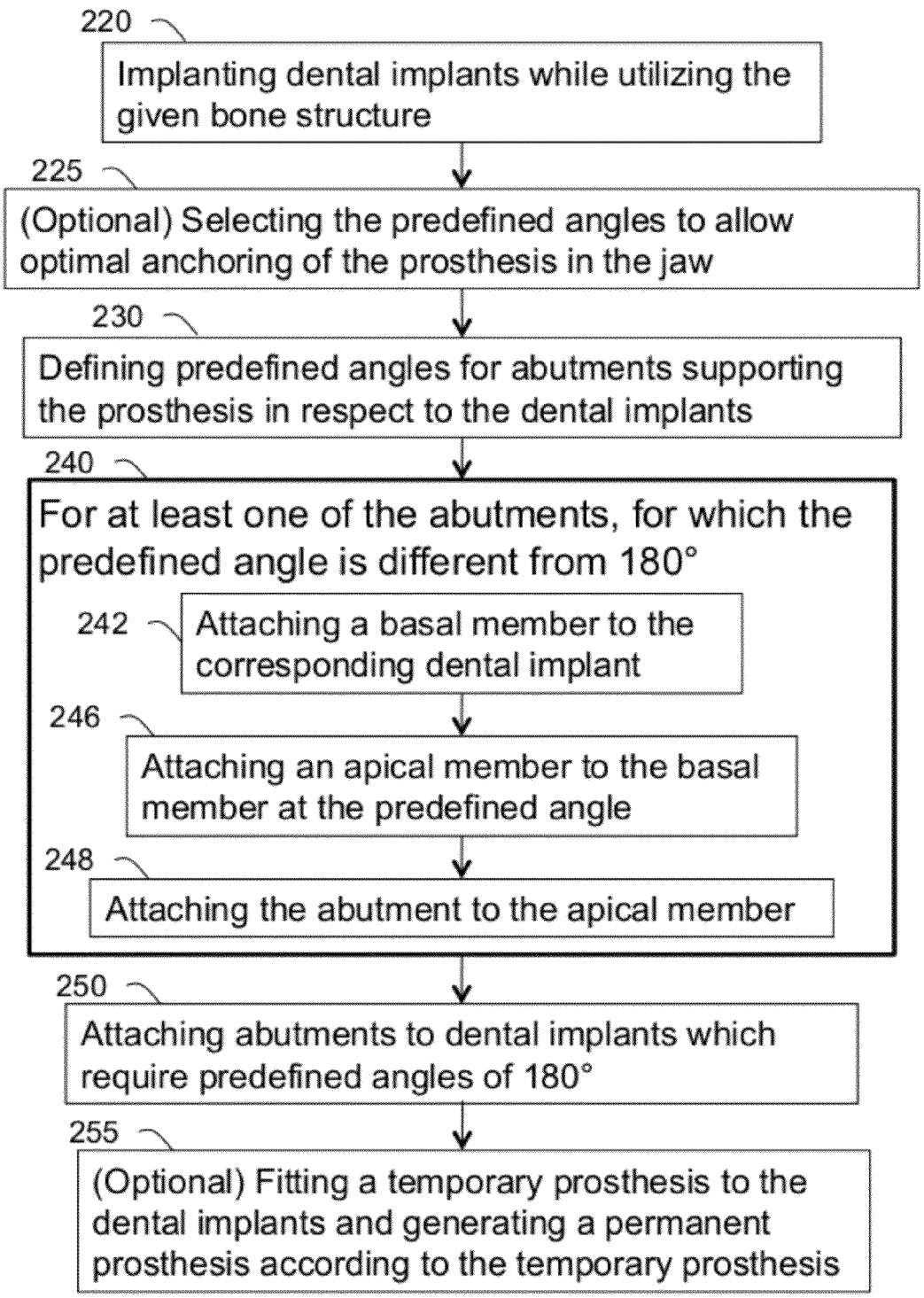
FIG. 6 is a high level schematic flowchart of a method of connecting a prosthesis to a jaw with a given bone structure, according to some embodiments of the invention.

FIG. 6 is a high level schematic flowchart of a method of connecting a prosthesis to a jaw with a given bone structure, according to some embodiments of the invention. The method comprises the stages: implanting a plurality of dental implant while utilizing the given bone structure (stage 220); defining predefined angles for a plurality of abutments supporting the prosthesis in respect to the dental implants (stage 230), such that each abutment corresponds to a dental implant; for at least one of the abutments, for which the predefined angle is different from 180° (stage 240); attaching a basal member to the dental implant (stage 242), the basal member comprising a distal inner thread exhibiting a first length axis; attaching an apical member to the basal member (stage 246), the apical member comprising a proximal outer thread corresponding to the distal inner thread of the basal member and exhibiting a second length axis upon the attaching (stage 246), wherein the second length axis forms the predefined angle in respect to the first length axis; and attaching the abutment to the apical member (stage 248). The method further comprises attaching abutments to dental implants which require predefined angles of 180° (stage 250). The method may further comprise applying fastening means to secure the basal member and/or the apical member.

According to some embodiments of the invention, the method further comprises selecting the predefined angles to allow optimal anchoring of the prosthesis in the jaw (stage 225), thereby allowing a high flexibility in selecting the predefined locations of the dental implants in respect to the jaw structure.

According to some embodiments of the invention, the method further comprises fitting a temporary prosthesis to the dental implants and generating a permanent prosthesis according to the temporary prosthesis (stage 255).

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of some embodiments of the invention shall not be construed as an admission that such reference is available as prior art to the present invention.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A compound angular joint for connecting an abutment to a dental implant in a predefined angle, the compound angular joint comprising:
   a basal member having a first length axis and comprising a basal member distal inner thread having a second length axis; and
   an apical member comprising an apical member distal inner thread, and a proximal outer thread corresponding to the basal member distal inner thread and exhibiting the second length axis upon connection thereto, wherein the apical member distal inner thread has a smaller diameter than the proximal outer thread, wherein the basal member has a hole having a predefined shape and going through the basal member, such that the basal member has an inner surface, wherein the hole allows proximally connecting the basal member to the dental implant by inserting an implant connector through the hole and connecting the implant connector to the dental implant, and wherein the basal member distal inner thread is located distally on the inner surface, and comprises at least two complete windings, wherein the predefined shape is selected such that it allows fastening the basal member to the dental implant by the implant connector, wherein the apical member distal inner thread is arranged to connect the abutment by an abutment connector distally to the apical member, wherein the apical member distal inner thread comprises at least two complete windings, such that the at least two complete windings allow securing the abutment to the apical member by the abutment connector, wherein the second length axis forms the predefined angle to the first length axis, and wherein the compound angular joint allows implanting a tooth prosthesis at the predefined angle wherein the predefined angle is smaller than 180° in respect to the dental implant.

2. The compound angular joint of claim 1, wherein the abutment connector is a screw and the implant connector is a screw.

3. The compound angular joint of claim 2, wherein the implant connector comprises a screw head, and wherein the predefined shape of the hole is selected to hold the screw head.

4. The compound angular joint of claim 1, wherein the basal member and the apical member are shaped to allow their connection when the basal member is connected to the dental implant by the implant connector.

5. The compound angular joint of claim 1, wherein the apical member distal inner thread further comprises fastening means arranged to resist loosening of contact between the abutment connector and the apical member distal inner thread.

6. The compound angular joint of claim 1, wherein the basal member distal inner thread further comprises fastening means arranged to resist loosening of contact between the proximal outer thread and the basal member distal inner thread.

7. The compound angular joint of claim 1, wherein the predefined angle is selected from: approximately 17°, and approximately 30°.

8. A system comprising:
an abutment,
a compound angular joint for connecting the abutment to a dental implant in a predefined angle, the compound angular joint comprising:
  a basal member having a first length axis and comprising a basal member distal inner thread having a second length axis; and
  an apical member comprising an apical member distal inner thread, and a proximal outer thread corresponding to the basal member distal inner thread and exhibiting the second length axis upon connection thereto,
wherein the basal member has a hole having a predefined shape and going through the basal member, such that the basal member has an inner surface, wherein the hole allows proximally connecting the basal member to the dental implant by inserting an implant connector through the hole and connecting the implant connector to the dental implant, and wherein the basal member distal inner thread is located distally on the inner surface and comprises at least two complete windings,
wherein the predefined shape is selected such that it allows fastening the basal member to the dental implant by the implant connector,
wherein the apical member distal inner thread is arranged to connect the abutment by an abutment connector distally to the apical member,
wherein the apical member distal inner thread comprises at least two complete windings, such that the at least two complete windings allow securing the abutment to the apical member by the abutment connector,
wherein the second length axis forms the predefined angle to the first length axis, and
wherein the compound angular joint allows implanting a tooth prosthesis at the predefined angle wherein the predefined angle is smaller than 180° in respect to the dental implant.

* * * * *